(12) United States Patent
Tanghoj

(10) Patent No.: US 7,867,220 B2
(45) Date of Patent: Jan. 11, 2011

(54) CATHETER ASSEMBLY WITH CATHETER HANDLE AND CONTAINER

(75) Inventor: Allan Tanghoj, Kokkedal (DK)

(73) Assignee: Coloplast A/S, Humlebaek (DK)

( * ) Notice: Subject to any disclaimer, the term of this patent is extended or adjusted under 35 U.S.C. 154(b) by 274 days.

(21) Appl. No.: 10/552,717

(22) PCT Filed: Apr. 7, 2004

(86) PCT No.: PCT/DK2004/000265

§ 371 (c)(1),
(2), (4) Date: Aug. 7, 2006

(87) PCT Pub. No.: WO2004/089454

PCT Pub. Date: Oct. 21, 2004

(65) Prior Publication Data

US 2007/0066963 A1    Mar. 22, 2007

(30) Foreign Application Priority Data

Apr. 11, 2003   (DK) ............................... 2003 00574

(51) Int. Cl.
*A61M 27/00* (2006.01)
(52) U.S. Cl. ...................... 604/544; 604/263
(58) Field of Classification Search ................ 604/544, 604/263, 513
See application file for complete search history.

(56) References Cited

U.S. PATENT DOCUMENTS

| | | | |
|---|---|---|---|
| 4,224,951 A | | 9/1980 | Hasson |
| 6,221,070 B1 * | 4/2001 | Tu et al. ....................... 606/41 |
| 6,355,004 B1 * | 3/2002 | Pedersen et al. ............ 600/581 |
| 6,415,823 B1 | 7/2002 | Vasek et al. |
| 2003/0004496 A1 | 1/2003 | Tanghoj |
| 2003/0018293 A1 * | 1/2003 | Tanghoj et al. ................ 604/19 |
| 2003/0018322 A1 | 1/2003 | Tanghoj et al. |
| 2008/0045921 A1 * | 2/2008 | Anderson et al. ........... 604/508 |

FOREIGN PATENT DOCUMENTS

| | | |
|---|---|---|
| DK | 172941 B1 | 3/1998 |
| EP | 1 090 656 A1 | 4/2001 |
| JP | 11 253548 | 3/1999 |
| WO | WO 98/11932 | 3/1998 |
| WO | WO 00/30575 | 6/2000 |
| WO | WO 03/002179 A2 | 1/2003 |

\* cited by examiner

*Primary Examiner*—Kevin C Sirmons
*Assistant Examiner*—Deanna K Hall
(74) *Attorney, Agent, or Firm*—Coloplast Corp., Coloplast A/S; Daniel G. Chapik; Nicholas R. Baumann

(57) ABSTRACT

A catheter assembly including a catheter handle and a catheter assembly with a catheter element and a container for accommodation of the catheter element. In a first compact configuration, the catheter element and the catheter handle are separated to reduce the length of the catheter assembly. The catheter element is in the container and the catheter handle is attached on the outside of the container assembly. The catheter handle can be detached and interlocked with the catheter element to constitute, in a second configuration, a catheter device.

22 Claims, 2 Drawing Sheets

CATHETER ASSEMBLY WITH CATHETER HANDLE AND CONTAINER

This is a nationalization of PCT/DK04/000265 filed Apr. 7, 2004 and published in English.

INTRODUCTION

The present invention relates to a catheter for draining bodily fluids, e.g. from the bladder. In particular, the invention relates to a catheter assembly comprising a container assembly, said container assembly comprising at least one catheter element. In a proximal end of the catheter element, the element is adapted for insertion in a urinary canal. The container assembly further comprises a container with a cavity adapted to accommodate at least a proximal section of said catheter element. The assembly further comprises a catheter handle adapted to be interlocked with said catheter element, the handle comprising a sleeve section adapted to surround a portion of said container.

BACKGROUND OF THE INVENTION

For a large group of persons intermittent catheterisation is a daily-life procedure, taking place several times a day. Typically catheters for intermittent catheterisation are used by patients suffering from urinary incontinence or by disabled individuals like para- or tetraplegics who may have no control permitting voluntary urination and for whom catheterisation may be the way of urinating. Using an intermittent catheter, the bladder may be drained through a natural or artificial urinary canal.

Existing catheters are designed to minimise the risk of sores in the mucous membrane and to give substantially no sensation of pain during insertion. Accordingly known catheters are typically provided with a smooth and slippery surface optimised for safe and comfortable insertion in the urinary canal.

The risk of urinary tract infections is a major problem for persons using intermittent catheterisation. Intermittent catheters are typically provided in sterile packing and in order to avoid contamination prior to use the catheter should preferably be handled without touching the insertable portion with the hands.

As many users of intermittent catheters have reduced dexterity, intermittent catheters should be easy to unwrap, prepare and handle in the catheterisation procedure.

Typically catheters are designed for one-time use and accordingly the costs for producing, packing and sterilising a catheter is an important issue.

The availability of catheter assemblies, which are compact and discrete to carry along and dispose via the garbage collection in addition to being easy to use, even for individuals with reduced dexterity, significantly improves quality of life for a large group of individuals.

WO03/002179 discloses a collapsible catheter set featuring a telescopic joint between a catheter handle and a catheter element with a proximal end adapted to be inserted in a urinary duct. The catheter element may have a hydrophilic coating and the cavity between the inner side of the handle and the outer side of the catheter element in collapsed position may be adapted to contain a liquid swelling medium for swelling said hydrophilic coating. Though handy to use the device is relatively complicated to manufacture and is dependent on delicate mechanic solutions to work as intended.

WO03/002179 also discloses a catheter set featuring a catheter element with a connector section and a handle element, wherein the catheter element and the handle element are separable. The handle element is adapted to accommodate the catheter element. Before use the catheter element is pulled out of the handle element and connected to the handle element to constitute a catheter device. The preparation of this catheter set requires some dexterity as the catheter element must be manipulated touching only the connector section, which is a small part of the catheter element.

In conclusion there is still a need for a catheter assembly, which is compact, simple to produce and simple to use, even for users with a reduced dexterity.

SUMMARY OF THE INVENTION

The invention relates to a catheter assembly of the kind mentioned in the introduction characterized in that said catheter handle is adapted to be separated from said catheter element and from said container. Since the handle is separable from the catheter element and from the container, the handle may be arranged onto the container in a way which facilitates a compact design for easy shipping and handling of the assembly until use. During use, the handle may be arranged onto the catheter element in a way which facilitates easy handing of the catheter element for insertion into urethra.

BRIEF DESCRIPTION OF THE DRAWINGS

The invention is disclosed more in detail with reference to the following drawings showing the principles of the invention (not drawn to scale).

Figure 1:
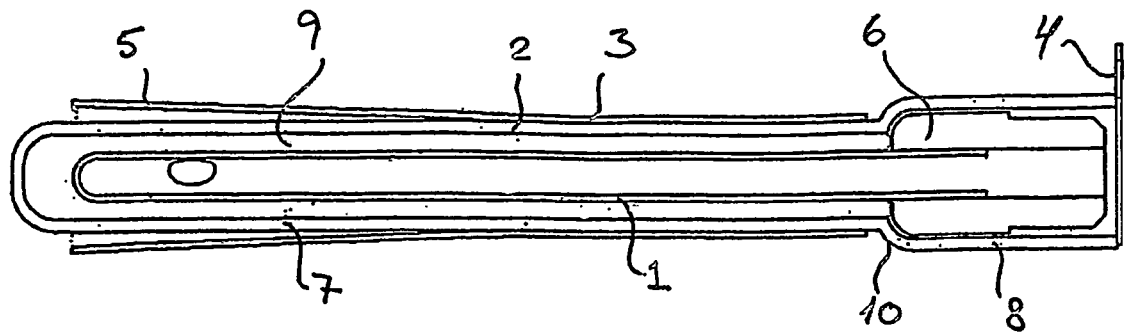
FIG. 1 shows a longitudinal section of one embodiment of the invention.

The principles concerning different parts of the embodiments may be combined in other ways than those shown in the drawings.

DETAILED DESCRIPTION OF THE INVENTION

The present invention relates to a catheter assembly comprising a container assembly, said container assembly comprising at least one catheter element, which has a proximal end adapted for insertion in a urinary canal and an opposite distal end, the container assembly further comprising a container with a cavity adapted to accommodate at least a proximal section of said catheter element, said catheter assembly further comprising a catheter handle adapted to be interlocked with the catheter element, the catheter handle comprising a sleeve section adapted to surround a portion of said container, said catheter handle being adapted to be separated from said catheter element and from the container. The container assembly could comprise additional components in addition to the catheter element and the container, and the handle could in general be separated from the container assembly as such.

After separation from the container assembly, the handle could be interlocked with the catheter element, e.g. to a distal end thereof, to facilitate handling thereof.

The catheter device comprising the catheter handle interlocked with the catheter element may be suitable for emptying the bladder through a natural or an artificial urinary canal.

In a first configuration of the elements of the catheter assembly of the invention, the sleeve section of the catheter handle is surrounding a portion of the container assembly, e.g. a portion of the container and/or a portion of the catheter. In a preferred embodiment of the invention the sleeve section of the catheter handle is adapted to surround at least a portion of the container. The handle may surround the container totally, e.g. forming a ring arranged around the container assembly. Alternatively, the handle may surround the container partially, e.g. forming a ring shaped body with a gap and being arranged around the container assembly. Furthermore the catheter handle is adapted to be separated from the container assembly in a second configuration and the catheter handle and the catheter element are adapted to be interlocked in a third configuration by connection means. In said third configuration the catheter assembly provides a device for urinary catheterisation comprising the catheter element and the catheter handle.

The invention relates to any form of urinary catheterisation including urethral and supra pubic catheterisation. The catheter element comprised in said device for urinary catheterisation is an elongated member with a proximal end adapted for insertion in a natural or artificial urinary duct of an individual, and an opposite distal end. The catheter element could be of any type, such as disclosed in WO03/002179. In addition to tubular catheters for which the drainage canal is bounded by the catheter material, the catheter assembly may comprise a catheter element of wing catheter type for which a part of the drainage canals is bounded by the urinary duct.

A catheter assembly according to the present invention is particularly advantageous for short catheters, used e.g. by females, children or persons with an artificial urinary canal. In one embodiment of the invention the catheter element is adapted to fit the female urethra, i.e. it may be provided in a length in the range of 50-200 mm, such as 130-180 mm, such as in a length in the size of 150 mm. In order to provide a catheter assembly which may be even more compact and discrete in the first configuration, the catheter element may even be provided in a length in the range of 50-90 mm, such as in the range 55-85 mm, such as in the range of 60-80 mm, such as a length in the size of 70 mm. In order to facilitate opening of the bladder, the catheter element and handle could be made with a smooth transition and with a size of at least a proximal end portion of the handle, i.e. towards the catheter when attached thereto, which thickness allows the user to insert at least this part of the handle into the urethra during use. For that purpose, the handle could be made with a shape and size when viewed in a cross-sectional view, which shape and size corresponds to the shape and size of the insertable part of the catheter element.

It is an aspect of the present invention to provide a catheter assembly, which the user can carry with her in a compact shape. The sleeve section of the catheter handle is adapted to surround a portion of the container assembly in a first configuration, which may reduce the size of the catheter assembly in said first configuration intended for storage of the catheter assembly.

The sleeve section of the catheter handle may comprise one or more extruded tubular members made e.g. by extrusion, inject moulding, blow moulding etc. or from one or more sheets curved to constitute a longitudinal section of an essentially tubular member or even welded together to form an essentially tubular member, such as a cylindrical member. Defining a cross section of an elongated element to be a cross section perpendicular to the long axis of that element, a cross section of the sleeve section of the catheter handle may be essentially circular, but could have any cross sectional shape, such as square, triangle, polygon etc. The cross section may be the same at any point along the catheter handle or it may change shape or area, having e.g. a conical part.

The catheter handle may be ergonomically shaped to make it easier to manipulate, especially for persons with reduced dexterity. The catheter handle may comprise gripping means constituted by protruding parts, grooves, rugged surfaces, finger holes etc.

The catheter handle may have connection means for connecting the handle to a bag for collecting bodily fluids. The connection means may e.g. comprise a conical distal section of the catheter handle.

For specific purposes, it may be advantageous to provide the catheter assembly with a relatively long handle, e.g. a handle, which is longer than the catheter element or even longer than the container assembly.

The catheter handle and the container assembly could extend primarily in one longitudinal direction, and in one embodiment of the invention the catheter handle is shorter than said container assembly in said longitudinal direction. The length of the catheter assembly in the first configuration may, in that case, equal the length of the container assembly. However, the catheter handle may also extend beyond the length of the container to jut over the container assembly. The catheter handle may, as an example, comprise a distal interlocking section, which is too narrow to surround the container assembly.

In a further embodiment of the invention the catheter handle is shorter than the catheter element. Especially for female users a relatively short handle may be advantageous, making the catheter device easier to manipulate without striking the toilet bowl.

In one embodiment of the invention, the catheter handle is adapted to be attached to the container assembly in a first configuration. The catheter handle may be attached to the container or to the catheter element. When attached to the container or to the catheter element, the handle and the container assembly constitute one component.

The catheter handle may be adapted to be reversibly attached to the container assembly. A reversible attachment may be obtained by mechanical means such as tight-fit, click locks, snap locks, screw locks etc or by surface contact means such as adhesive bonding, magnetic locking, hook and loop locking, etc. A reversible attachment may even be a loose fit with some clearance between the catheter handle and the container assembly, but wherein the parts are joined to constitute one component. In another embodiment, the container, the catheter element and the handle is joined by arranging all three components in a sealed bag.

The catheter handle could also be adapted to be irreversibly attached to the container assembly, e.g. by irreversible click or snap locks. The catheter handle and a part of the container assembly may even be made as a coherent unit, e.g. by moulding or adhesive bonding. The catheter handle and the container assembly may be irreversibly separated by means of breakable connections, weakness zones, etc.

The catheter handle and the catheter element are adapted to be interlocked in a third configuration by interlocking means. The interlocking means are adapted to establish a connection between the catheter handle and the catheter element, which allows the user to manipulate the catheter element by manipulation of the catheter handle. The interlocking means may comprise one or more additional catheter sections adapted to link the catheter element and the catheter handle.

The interlocking means may be designed so that the user has the option of connecting an extension hose or a urine bag to the catheter element, rather than using the catheter handle.

The interlocking means may be irreversible but could also be adapted to be reversible, allowing the catheter element and the catheter handle to be separated after use, i.e. after having been in said third configuration. It is an advantage that the waste after catheterisation is handy for disposal or even for the user to carry with her if necessary. Hence it may be an advantage that the catheter device can be disconnected and reassembled in a more compact configuration, e.g. essentially the first configuration.

The interlocking means may for example comprise mechanical means, such as tight-fit, click locks, snap locks, screw locks etc, or surface contact means such as adhesive bonding or magnetic lock.

In one embodiment of the invention, the container is an elongated member, which is closed in a proximal end. The container may comprise tubular parts made e.g. by extrusion, inject moulding, blow moulding etc. The container may also comprise one or more sheets of a suitable material welded together. The tubular members may have an essentially circular cross section, but could have any cross sectional shape or even be flexible. In order to facilitate a firm grip, the container may have gripping means.

In a preferred embodiment of the invention the container comprises sealing means for sealing said cavity. The sealing means may be adapted to releasably seal a distal opening of the container. The sealing means may be adapted to be removed by hand and may be ergonomically shaped or comprising gripping means facilitating their removal. The sealing means could also be adapted to be broken or removed by an element of the catheter assembly. For example, the container assembly may be sealed by a foil and the catheter handle may be adapted to penetrate said foil, e.g. using the principle known from straws with an obliquely cut end suitable for pricking hole in a foil.

The sealing means may be irreversible such as welding, weakness zones, breakable foils, tear-off flaps, lids, etc. Reversible sealing means such as plugs, lids, screw caps etc, are advantageous to provide sealed handy waste after catheterisation. The catheter element and the catheter handle may constitute at least a part of said sealing means.

In the process of interlocking the catheter handle and the distal end of the catheter element, the proximal end of the catheter element is typically pressed towards the proximal end of the container. It may hence be an advantage to provide means to hold back the catheter element in order to facilitate the interlocking of the catheter handle with the distal end of the catheter element. Furthermore, when the catheter element has a hydrophilic coating it may be desirable to protect the tip of the catheter by providing the container assembly with means adapted to restrict displacement of the catheter element towards the proximal end of the container.

In a preferred embodiment of the invention a distal section of the catheter element has at least one radially outwardly protruding part and a proximal compartment of the cavity is adapted to accommodate a proximal section of the catheter, said proximal compartment having a distal opening zone with exclusion means adapted to exclude said distal section of the catheter element from entering the proximal compartment.

The force applied to the catheter element by pressing the catheter handle against it will tend to push the catheter in a proximal direction. When the container is held firmly by a user, the force tending to push the catheter in a proximal direction may be counteracted by a force transmitted from the container to the catheter via said protruding part bearing on said exclusion means.

For safety reasons a further advantage of providing said distal section of the catheter element with substantially protruding parts, is to prevent the distal end of the catheter from escaping into the urethral opening, even if the user has failed to interlock the catheter handle and the catheter element properly, so that the handle is unintentional detached from the catheter element during catheterisation.

The exclusion means are adapted to exclude said distal section of the catheter element from entering the proximal compartment by providing said distal opening zone of the cavity with a cross section, which is smaller or has a different shape or orientation than a cross section of the distal section of the catheter element, so as to keep back the protruding part when the catheter element is moved towards the proximal end of the container. The exclusion means may thus be in the shape of shoulders on the inside of the container. The shoulders may constitute a narrow part of a longitudinal cross-section of the container. The narrow part is typically situated in the distal end of the cavity or at least in closer vicinity to the distal end of the cavity than the proximal end of the cavity In one embodiment of the invention the exclusion means comprises an inwardly extending protrusion, e.g. a flange in the distal end of the cavity or at least in closer vicinity to the distal end of the cavity than the proximal end of the cavity. The inward protrusion could be adapted to narrow the cavity in said opening zone. The narrowing should be such as to leave a passage of a size and shape adapted to allow the proximal portion of the catheter element to pass through, but exclude the outward protruding part of the catheter element.

The inward protrusion may be placed in a distance from the distal end of the cavity to allow room for the outward protruding part in the container but the inward protrusion may also be placed in the distal end of the cavity. Typically the inward protrusion is placed closer to the distal end than to the proximal end of the cavity.

A container according to this embodiment of the invention may be made from one essentially rigid tubular member, with the inward protrusion placed in said cavity such that said distal section of said catheter element is excluded from the cavity. Another container according to this embodiment is flexible; it could even be as flexible as a regular plastic bag, while the inward protrusion is an essentially rigid part of the container.

In one embodiment of the invention, the container comprises two essentially rigid tubular members, such that a first tubular member defines said proximal compartment with a first cross section and a second tubular member defines a distal section of the cavity with a second cross section, the tubular members being connected such that said distal section of said catheter element is prevented from passing from the distal section of the cavity to the proximal compartment. The cross sections of the first and second tubular members may be essentially circular, the diameter of said first tubular member being smaller than the diameter of said second tubular member. Due to the narrowing of the outside diameter of the container it is possible for a catheter handle to have a cross section, which is sufficiently narrow to engage the distal section of the catheter element in the distal section of the container, and sufficiently wide to surround the proximal section of the container.

In another embodiment of the invention at least a part of said opening zone is flexible. The flexibility allows the cross section of the opening zone to change size or shape by application of finger pressure, such that the distal section of the catheter element is prevented from passing the opening zone. A flexible container may be provided with clamping means as known from prior art to enhance the finger pressure. The opening zone may be plastic deformable with some or none shape memory or the opening zone may comprise non-rigid zones which are flexible like a plastic bag.

For simple production it may be an advantage to use the same material for a major part of the entire container although the flexibility may be required only in the opening zone. The container may be made of a tubular element with a flexibility allowing the cross section to elongate by application of finger pressure, such that at least one diameter of the cross section is reduced. In another embodiment of the invention the container is made from at least one sheet of a flexible material joined along edges to constitute an elongated plastic bag like container.

The interlocking means may comprise a snap lock, which require very little applied force to firmly interlock the catheter handle with the catheter element. Hence, a catheter assembly according to the invention may comprise a catheter element without a protruding part, in which case the catheter assembly can be slimmer.

In a preferred embodiment the container assembly comprises sealing means for sealing said cavity. The container assembly may thus comprise at least one sealed cavity. Accordingly, the catheter assembly may further comprise a lubricating medium such as a gel or water for activating a hydrophilic coating of the catheter element. The lubricating medium could be contained in the container assembly between the container and the catheter element.

The catheter assembly may comprise one or more active ingredients, such as anti-bacterial agents to reduce the risk of infections or active agents for localized treatment of the urinary tract system. The active ingredients may e.g. be provided in a liquid solution or as a solid.

In one embodiment of the invention the catheter element is adapted for lubrication prior to use, e.g. by a lubricating gel or by means of a hydrophilic coating, which is swelled by a swelling medium, and the container is adapted to contain a lubricating substance such as a liquid swelling medium or a gel intended to reduce the friction between the catheter element and the tissue.

In a preferred embodiment of the invention at least a portion of the catheter element has a hydrophilic coating. The hydrophilic coating is adapted to provide a slippery surface on the catheter when treated with a liquid swelling medium.

A catheter element with a hydrophilic coating may be treated with water from the tap or with a liquid swelling medium provided separately or as a part of the catheter assembly. In one embodiment of the invention, the container is liquid tight and may e.g. be adapted to contain a liquid swelling medium for swelling said hydrophilic coating. Typically, swelling of the hydrophilic coating is not instant, hence it is advantageous to provide the catheter element pre swelled and ready to use by storing at least a proximal part of the catheter element in contact with the liquid swelling medium in the container. Alternatively, or in combination with the hydrophilic surface, the assembly could be provided with a pouch containing a lubricating gel or the catheter element, or at least an insertable part thereof, could be pre-lubricated by a gel.

A further aspect of the invention is to provide a method for preparing a catheter device, said method comprising the steps of:

a) providing a catheter assembly comprising a container assembly, said container assembly comprising a catheter element, which has a proximal end adapted for insertion in a urinary canal and an opposite distal end, the container assembly further comprising a container with a cavity adapted to accommodate at least a proximal section of said catheter element and a catheter handle comprising a sleeve section adapted to surround a portion of said container b) separating the catheter handle from the container assembly c) connecting the catheter handle to the catheter element.

d) removing the catheter element from the container.

DESCRIPTION OF THE PREFERRED EMBODIMENTS

The invention is now explained more in detail with reference to the drawings showing embodiments of the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

FIG. 1 shows a longitudinal section of a preferred embodiment of the invention, with a catheter element (1), a container (2) and a catheter handle (3) in a first configuration, wherein the catheter element is in the container, which is sealed with a tear-off flap (4) and the catheter handle is surrounding a portion of the container. The catheter handle in one end has a conical section (5) adapted to be connected to a urine bag, while the opposite end is adapted to be interlocked with the distal end of the catheter element. The catheter element has a distal section with a protruding part (6). The container comprises a first tubular section (7) and a second tubular section (8), both of which having an essentially circular cross section. The second tubular section (8) has a diameter allowing this section to accommodate the protruding part (6) of the catheter element (1), while the diameter of the first tubular section is too narrow to accommodate the protruding part and defines a proximal compartment (9), adapted to exclude the protruding part of the catheter element.

Figure 2:
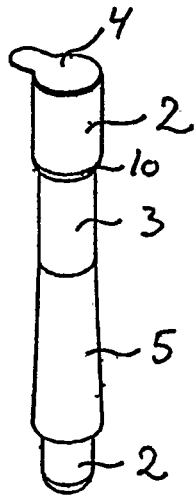
FIGS. 2-4 shows the same embodiment of the invention in three different configurations.

FIG. 2 shows the catheter assembly of FIG. 1 from the outside, where the visible parts are the catheter handle (3) with the conical section (5), the first tubular section (7) and the second tubular section (8) of the container (2) and the tear-off flap (4).

Figure 3:
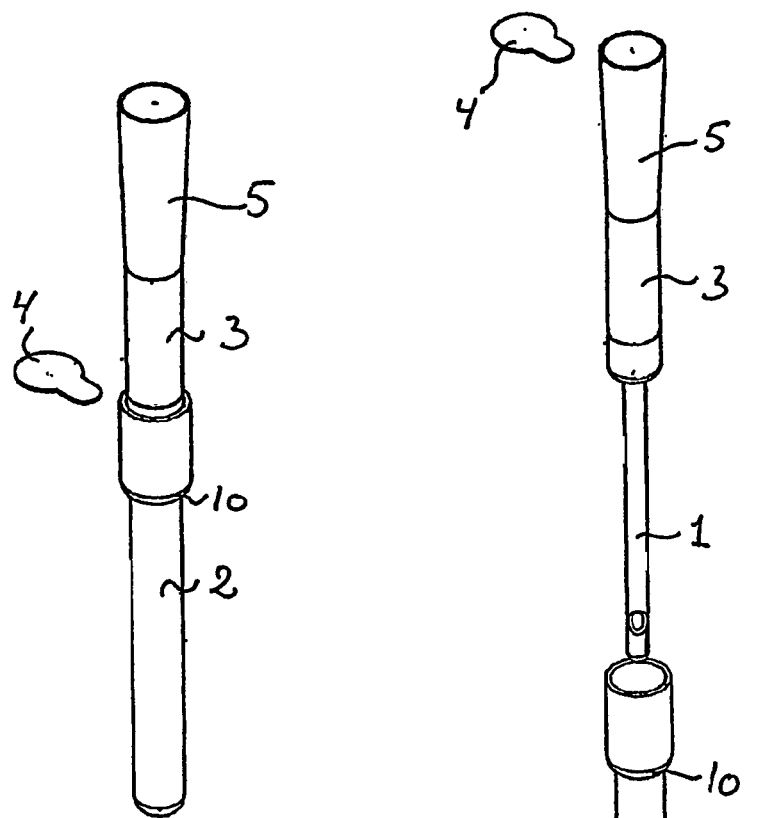

FIG. 3 shows the catheter assembly of FIG. 1, in a position where the catheter handle has been detached from the container assembly, the tear-off flap (4) has been removed and the catheter handle (3) has been interlocked with the catheter element (1) in the container (2) to constitute a catheter device.

Figure 4:
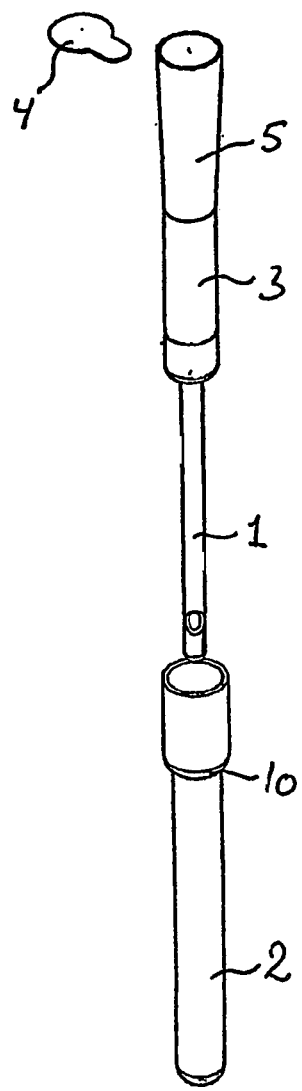

FIG. 4 shows the catheter assembly of FIG. 1, in a position where the catheter device is pulled out of the container (2).

Figure 5:
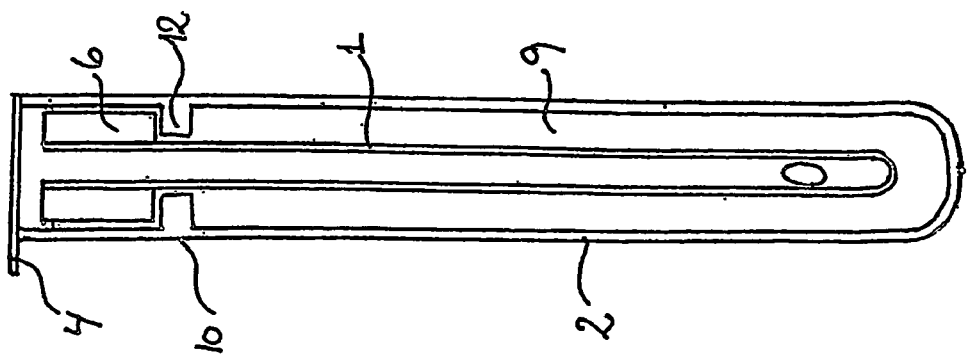
FIGS. 5-8 shows longitudinal sections of the container assembly of other embodiments of the invention.

FIG. 5 shows the container assembly of another embodiment of the invention, wherein the proximal compartment (9) and the distal section of the cavity has essentially the same cross section, but the opening zone (10) comprises a flange (12) adapted to exclude the protruding part of the catheter element from the proximal compartment (9). In this embodiment of the invention the catheter handle may comprise a section adapted to surround a proximal section of the container and an interlocking section, which extends beyond the container.

Figure 6:
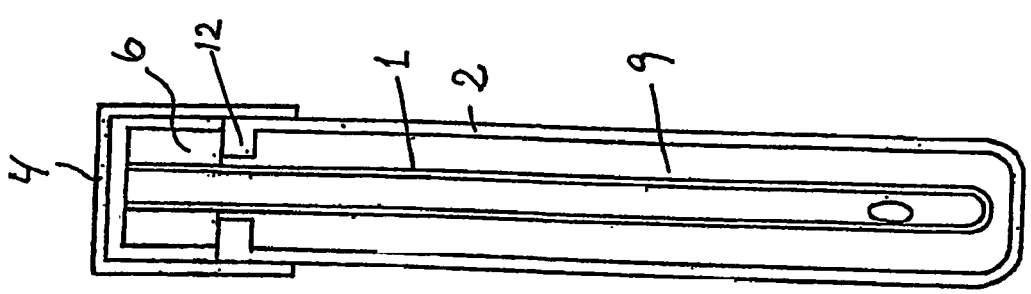

FIG. 6 shows the container assembly of another embodiment of the invention, wherein a flange (12) is placed in a distal end of the container cavity. The container is sealed by means of a lid (13). The lid and the catheter handle may be the same element, having interlocking means adapted to engage the catheter element and a suitable length and an outlet for the urine flow and sealing means for sealing the outlet when the element is used as lid.

Figure 7:
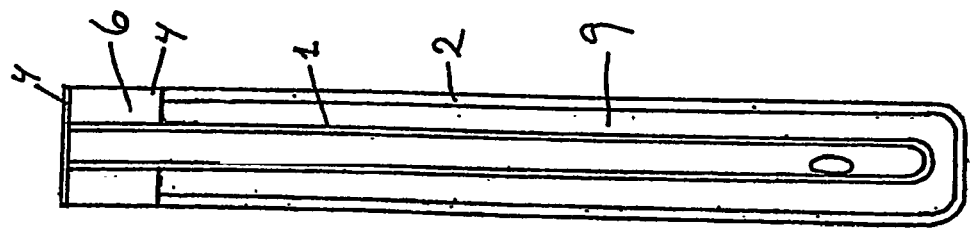

FIG. 7 shows the container assembly of another embodiment of the invention, wherein the container (2) is made of one tubular part, which is too narrow to accommodate the protruding part of the catheter element (6). The distal open end of the container is sealed by means of the catheter element (1) and sealing means for sealing the outlet of the catheter element (1).

Figure 8:
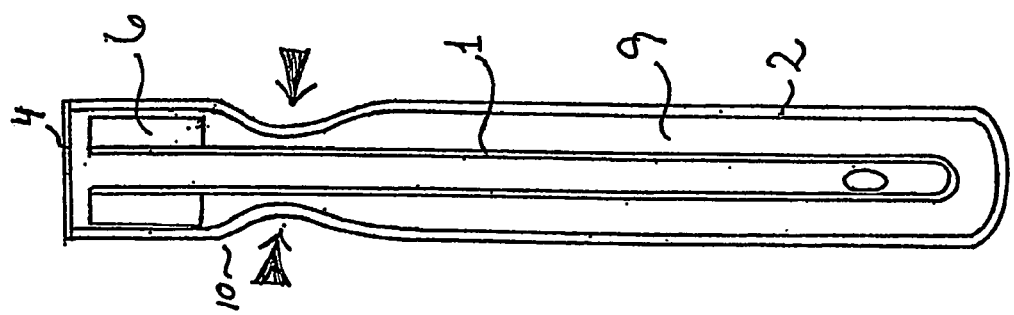

FIG. 8 shows the container assembly of another embodiment of the invention, wherein the container (2) comprises a flexible zone (14), adapted to reshape the opening zone (10) so as to exclude the protruding part (6) from the proximal compartment (9). The entire container may be flexible so that the walls of the container can be compressed to fit in the handle.

Figure 9:
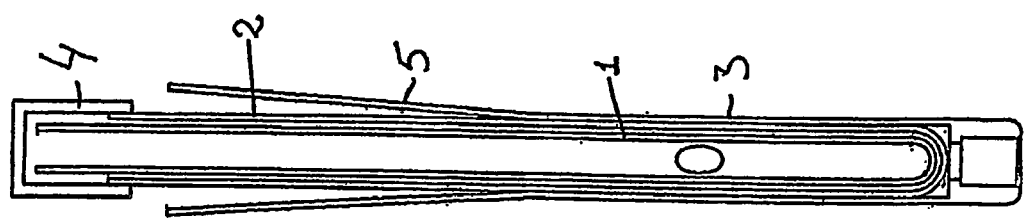
FIG. 9 shows longitudinal sections of other embodiments of the invention.

FIG. 9 shows a longitudinal section of another embodiment of the invention, with a catheter element (1), a container (2) and a catheter handle (3) in a first configuration, wherein the catheter element is in the container, which is sealed with a lid (4) and the catheter handle (3) is surrounding a portion of the container assembly. The catheter handle in one end has a conical section (5) adapted to be connected to a urine bag, while the opposite end, which jut out over the container assembly, is adapted to be interlocked with the distal end of the catheter element.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A catheter assembly comprising a container, a catheter handle having a first interlocking mechanism and at least one catheter element with a proximal end adapted for insertion in a urinary canal and an opposite distal end and having a second interlocking mechanism, the container having a first section adapted to accommodate at least a proximal section of said catheter element and a second section adapted to accommodate a distal section of said catheter element and a zone between the first section and the second section that is adapted to exclude entry of said distal section of said catheter element into said first section, said catheter handle adapted to be interlocked with the catheter element via engagement of the first interlocking mechanism with the second interlocking mechanism of the catheter element so that the catheter handle and the catheter element are mechanically locked together, the catheter handle further including a sleeve section adapted to surround a portion of said container, said catheter handle is configured to be detached from said catheter element and from said container.

2. The catheter assembly according to claim 1, wherein said catheter handle is adapted to be attached to said container assembly.

3. The catheter assembly according to claim 1, wherein said catheter handle is shorter than said container or shorter than said catheter element.

4. The catheter assembly according to claim 1, wherein said distal section of said catheter element has at least one protruding part and wherein a proximal compartment of a cavity of said container has a distal opening zone providing an exclusion element adapted to exclude said distal section of said catheter element from entering said proximal compartment.

5. The catheter assembly according to claim 4, wherein said exclusion element includes a radially inwardly extending protrusion in the cavity.

6. The catheter assembly according to claim 4, wherein at least a part of said distal opening zone is flexible.

7. The catheter assembly according to claim 1, further comprising a lubricating medium.

8. The catheter assembly according to claim 1, wherein at least a portion of said catheter element has a hydrophilic coating.

9. The catheter assembly according to claim 1, wherein said container includes a sealing means element for sealing said cavity.

10. A method for preparing a catheter device, said method comprising the steps of:
a) providing a catheter assembly having a container assembly, including a catheter element and a container having a first section adapted to accommodate a proximal section of said catheter element and a second section adapted to accommodate a distal section of said catheter element and a zone between the first section and the second section that is adapted to exclude entry of said distal section of said catheter element into said first section, and a catheter handle having a sleeve section surrounding a portion of said container;
b) detaching the catheter handle from the container assembly and from the catheter element;
c) connecting the catheter handle to the catheter element in a different position from that in which the sleeve section surrounded the portion of said container so that the catheter handle and the catheter element are mechanically locked together via an interlocking mechanism; and
d) removing the catheter element from the container.

11. The method as set forth in claim 10, wherein said step of detaching the catheter handle includes removing the sleeve section from around the container portion and the step of connecting includes interlocking a proximal end of said handle with the distal end of said catheter element.

12. The method as set forth in claim 11, further comprising the step of removing the catheter handle from the catheter element after catheterization.

13. The catheter assembly according to claim 1, wherein said catheter handle is adapted to be coupled with said assembly in two different configurations, movement of said catheter handle from a first configuration to a second configuration being effected by detaching said catheter handle from both said catheter element and said container.

14. The catheter assembly according to claim 13, wherein said sleeve section surrounds a portion of said container in said first configuration and is interlocked with said catheter element in a substantially linear arrangement therewith in said second configuration, said catheter handle when detached defining a third configuration in which said catheter handle is physically separate from both said container and said catheter element.

15. The catheter assembly according to claim 4, wherein a distal end of said sleeve section is smaller in diameter than said protruding part of said catheter element and is adjacent a proximal side of said protruding part in said first configuration and adjacent a distal side of said protruding part in said second configuration.

16. A catheter assembly comprising: catheter element with a proximal end adapted for insertion into a urinary canal and an opposite distal end, and a container having a first section adapted to accommodate said proximal end of said catheter element and a second section adapted to accommodate said distal end of said catheter element and a zone between the first section and the second section that is adapted to exclude entry of a distal section of said catheter element into said first section; and a catheter handle having a sleeve section and being adapted, in a first configuration, to be attached to said container assembly with said sleeve section surrounding a portion of said container and, in a second configuration, to be interlocked with said catheter element via an interlocking mechanism so that the catheter handle and the catheter element arc mechanically locked together in a substantially linear arrangement.

17. The catheter assembly according to claim 16, wherein said distal section of said catheter element has at least one protruding part and wherein a proximal compartment of a cavity of said container is adapted to accommodate a proximal section of said catheter, said proximal compartment having a distal opening zone with an exclusion element adapted to exclude said distal section of said catheter element from entering said proximal compartment.

18. The catheter assembly according to claim 17, wherein a distal end of said sleeve section is smaller in diameter than said protruding part of said catheter element and is adjacent a proximal side of said protruding part in said first configuration and adjacent a distal side of said protruding part in said second configuration.

19. The catheter assembly according to claim 17, wherein said exclusion element includes a radially inwardly extending protrusion in the cavity.

20. The catheter assembly according to claim 17, wherein at least a part of said distal opening zone is flexible.

21. The catheter assembly according to claim 16, wherein said catheter handle is configured to be physically detached from said catheter element and from said container when moved from said first configuration to said second configuration.

22. A catheter assembly comprising:
a catheter element having a proximal end adapted for insertion into a urinary canal;
a container having a first section adapted to accommodate a proximal section of said catheter element and a second section adapted to accommodate a distal section of said catheter element and a zone between the first section and the second section that is adapted to exclude entry of said distal section of said catheter element into said first section; and
a catheter handle disposed around said second section of said container, said catheter handle detachable from said container and attachable to said distal section of said catheter element, said catheter handle further detachable from said catheter element.

* * * * *